United States Patent
Drochner et al.

(10) Patent No.: US 10,682,154 B2
(45) Date of Patent: Jun. 16, 2020

(54) CUTTING MECHANISMS FOR SURGICAL END EFFECTOR ASSEMBLIES, INSTRUMENTS, AND SYSTEMS

(71) Applicant: COVIDIEN LP, Mansfield, MA (US)

(72) Inventors: Thomas E. Drochner, Longmont, CO (US); David J. Van Tol, Boulder, CO (US); Duane E. Kerr, Loveland, CO (US); Gary M. Couture, Ward, CO (US); James D. Allen, IV, Broomfield, CO (US); Robert M. Sharp, Boulder, CO (US)

(73) Assignee: Covidien LP, Mansfield, MA (US)

( * ) Notice: Subject to any disclaimer, the term of this patent is extended or adjusted under 35 U.S.C. 154(b) by 347 days.

(21) Appl. No.: 15/642,858

(22) Filed: Jul. 6, 2017

(65) Prior Publication Data
US 2018/0036025 A1 Feb. 8, 2018

Related U.S. Application Data

(60) Provisional application No. 62/369,958, filed on Aug. 2, 2016.

(51) Int. Cl.
*A61B 17/295* (2006.01)
*A61B 18/14* (2006.01)
(Continued)

(52) U.S. Cl.
CPC ........ *A61B 17/295* (2013.01); *A61B 18/1445* (2013.01); *A61B 17/285* (2013.01);
(Continued)

(58) Field of Classification Search
CPC ..... A61B 17/285; A61B 17/29; A61B 17/295; A61B 18/1445; A61B 2017/00353;
(Continued)

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| DE | 2415263 A1 | 10/1975 |
| DE | 02514501 A1 | 10/1976 |

(Continued)

OTHER PUBLICATIONS

Michael Choti, "Abdominoperineal Resection with the LigaSure Vessel Sealing System and LigaSure ; Atlas 20 cm Open Instrument"; Innovations That Work, Jun. 2003.
(Continued)

*Primary Examiner* — Elizabeth Houston
*Assistant Examiner* — Mohamed G Gabr
(74) *Attorney, Agent, or Firm* — Carter, DeLuca & Farrell, LLP

(57) ABSTRACT

An end effector assembly configured for use with a surgical instrument or surgical system includes first and second jaw members each including an outer jaw housing, a tissue-treating plate, and a longitudinally-extending channel therethrough. At least one of the first or second jaw members is pivotable relative to the other between a spaced-apart position and an approximated position. A cutting mechanism is configured to cut tissue grasped between the jaw members. The cutting mechanism may include an activation member coupled to a knife and configured to advance the knife transversely between the jaw members, a heat-activated elongated sheet configured to un-roll to advance a cutting edge thereof transversely between the jaw members, or a clutch and spring mechanism configured to deploy a knife longitudinally between the jaw members.

6 Claims, 6 Drawing Sheets

(51) Int. Cl.
  *A61B 17/29* (2006.01)
  *A61B 17/072* (2006.01)
  *A61B 17/285* (2006.01)
  *A61B 17/00* (2006.01)
  *A61B 17/32* (2006.01)

(52) U.S. Cl.
  CPC ..... *A61B 17/29* (2013.01); *A61B 2017/00353* (2013.01); *A61B 2017/00367* (2013.01); *A61B 2017/07285* (2013.01); *A61B 2017/2926* (2013.01); *A61B 2017/320052* (2013.01); *A61B 2018/1455* (2013.01)

(58) Field of Classification Search
  CPC ........... A61B 2017/00367; A61B 2017/07285; A61B 2017/2926; A61B 2017/320052; A61B 2018/1455
  See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| D402,028 S | 12/1998 | Grimm et al. |
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| 6,656,175 B2 | 12/2003 | Francischelli et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,070,597 B2 | 7/2006 | Truckai et al. |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,491,202 B2 | 2/2009 | Odom et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 8,070,748 B2 | 12/2011 | Hixson et al. |
| 8,092,451 B2 | 1/2012 | Schechter et al. |
| 8,112,871 B2 | 2/2012 | Brandt et al. |
| 8,133,254 B2 | 3/2012 | Dumbauld et al. |
| 8,162,965 B2 | 4/2012 | Reschke et al. |
| 8,187,273 B2 | 5/2012 | Kerr et al. |
| 8,215,182 B2 | 7/2012 | Artale et al. |
| 8,257,352 B2 | 9/2012 | Lawes et al. |
| 8,266,783 B2 | 9/2012 | Brandt et al. |
| 8,277,446 B2 | 10/2012 | Heard |
| 8,287,536 B2 | 10/2012 | Mueller et al. |
| 8,292,067 B2 | 10/2012 | Chowaniec et al. |
| 8,292,886 B2 | 10/2012 | Kerr et al. |
| 8,298,233 B2 | 10/2012 | Mueller |
| 8,323,310 B2 | 12/2012 | Kingsley |
| 8,343,150 B2 | 1/2013 | Artale |
| 8,343,151 B2 | 1/2013 | Siebrecht et al. |
| 8,348,948 B2 | 1/2013 | Bahney |
| 8,357,159 B2 | 1/2013 | Romero |
| 8,388,647 B2 | 3/2013 | Nau, Jr. et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,876 B2 | 4/2013 | Kappus et al. |
| 8,430,877 B2 | 4/2013 | Kerr et al. |
| 8,439,911 B2 | 5/2013 | Mueller |
| 8,439,913 B2 | 5/2013 | Horner et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,512,371 B2 | 8/2013 | Kerr et al. |
| 8,540,749 B2 | 9/2013 | Garrison et al. |
| 8,556,929 B2 | 10/2013 | Harper et al. |
| 8,568,397 B2 | 10/2013 | Horner et al. |
| 8,568,412 B2 | 10/2013 | Brandt et al. |
| 8,585,736 B2 | 11/2013 | Horner et al. |
| 8,597,295 B2 | 12/2013 | Kerr |
| 8,623,018 B2 | 1/2014 | Horner et al. |
| 8,641,712 B2 | 2/2014 | Couture |
| 8,641,713 B2 | 2/2014 | Johnson et al. |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,115 B2 | 3/2014 | Reschke |
| 8,734,445 B2 | 5/2014 | Johnson et al. |
| 8,740,898 B2 | 6/2014 | Chojin et al. |
| 8,795,269 B2 | 8/2014 | Garrison |
| 8,808,288 B2 | 8/2014 | Reschke |
| 8,814,864 B2 | 8/2014 | Gilbert |
| 8,858,553 B2 | 10/2014 | Chojin |
| 8,888,775 B2 | 11/2014 | Nau, Jr. et al. |
| 8,945,125 B2 | 2/2015 | Schechter et al. |
| 8,961,504 B2 | 2/2015 | Hoarau et al. |
| 8,968,357 B2 | 3/2015 | Mueller |
| 8,968,358 B2 | 3/2015 | Reschke |
| 8,968,359 B2 | 3/2015 | Kerr et al. |
| 9,005,200 B2 | 4/2015 | Roy et al. |
| 9,017,372 B2 | 4/2015 | Artale et al. |
| 9,024,237 B2 | 5/2015 | Bonn |
| 9,028,495 B2 | 5/2015 | Mueller et al. |
| 9,060,798 B2 | 6/2015 | Harper et al. |
| 9,192,430 B2 | 11/2015 | Rachlin et al. |
| 9,498,278 B2 | 11/2016 | Couture et al. |
| 9,585,709 B2 | 3/2017 | Krapohl |
| 9,655,672 B2 | 5/2017 | Artale et al. |
| 9,820,806 B2 | 11/2017 | Lee et al. |
| 2003/0018332 A1 | 1/2003 | Schmaltz et al. |
| 2004/0073238 A1 | 4/2004 | Makower |
| 2004/0073256 A1 | 4/2004 | Marchitto et al. |
| 2004/0210282 A1 | 10/2004 | Flock et al. |
| 2004/0243125 A1 | 12/2004 | Dycus et al. |
| 2008/0045947 A1 | 2/2008 | Johnson et al. |
| 2008/0065128 A1* | 3/2008 | Ezzat .................. A61B 17/072 606/167 |
| 2008/0319442 A1* | 12/2008 | Unger ................ A61B 18/1445 606/48 |
| 2010/0042140 A1 | 2/2010 | Cunningham |

(56) References Cited

U.S. PATENT DOCUMENTS

| | | | |
|---|---|---|---|
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0249776 A1 | 9/2010 | Kerr | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0060356 A1 | 3/2011 | Reschke et al. | |
| 2011/0071523 A1 | 3/2011 | Dickhans | |
| 2011/0270245 A1 | 11/2011 | Horner et al. | |
| 2011/0270251 A1 | 11/2011 | Horner et al. | |
| 2011/0276049 A1 | 11/2011 | Gerhardt | |
| 2011/0295313 A1 | 12/2011 | Kerr | |
| 2012/0041438 A1 | 2/2012 | Nau, Jr. et al. | |
| 2012/0059372 A1 | 3/2012 | Johnson | |
| 2012/0059409 A1 | 3/2012 | Reschke et al. | |
| 2012/0095460 A1* | 4/2012 | Rooks .................... | A61B 17/28 606/45 |
| 2012/0296332 A1 | 11/2012 | Chernov et al. | |
| 2014/0214030 A1 | 7/2014 | Horlle | |

FOREIGN PATENT DOCUMENTS

| | | |
|---|---|---|
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 10045375 A1 | 4/2002 |
| DE | 102004026179 | 12/2005 |
| DE | 202007009317 U1 | 10/2007 |
| EP | 1159926 A2 | 12/2001 |
| EP | 1693008 A1 | 8/2006 |
| JP | 61-501068 | 9/1984 |
| JP | 5-5106 | 1/1993 |
| JP | 540112 | 2/1993 |
| JP | H06-502328 A | 3/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 1024051 | 1/1998 |
| JP | 11-070124 A | 3/1999 |
| JP | 11-169381 A | 6/1999 |
| JP | 11244298 | 9/1999 |
| JP | 2000-102545 A | 4/2000 |
| JP | 2000342599 A | 12/2000 |
| JP | 2000350732 A2 | 12/2000 |
| JP | 2001-008944 A | 1/2001 |
| JP | 2001-029356 A | 2/2001 |
| JP | 2001128990 A | 5/2001 |
| SU | 401367 A1 | 10/1973 |
| WO | 0036986 A1 | 6/2000 |
| WO | 0154604 A1 | 8/2001 |
| WO | 05110264 A3 | 4/2006 |
| WO | 2009029065 A1 | 3/2009 |

OTHER PUBLICATIONS

Chung et al., "Clinical Experience of Sutureless Closed Hemontoidectomy with LigaSure"; Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy"; Sales/Product Literature; Jan. 2004.

E. David Crawford "Evaluation of a New Vessel Sealing Device in Urologic Cancer Surgery"; Sales/Product Literature 2000.

Johnson et al. "Evaluation of the LigaSure Vessel Sealing System in Hemorrhoidectormy"; American College of Surgeons (ACS) Clinicla Congress Poster (2000).

Muller et al., "Extended Left Hemicolectomy Using the LigaSure Vessel Sealing System"; Innovations That Work, Sep. 1999.

Kennedy et al. "High-burst-strength, feedback-controlled bipolar vessel sealing"; Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery"; Innovations That Work, Jun. 2002.

Heniford et al. "Initial Research and Clinical Results with an Electrothermal Bipolar Vessel Sealer"; Oct. 1999.

Heniford et al. "Initial Results with an Electrothermal Bipolar Vessel Sealer"; Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents"; Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy"; Innovations That Work, Nov. 2002.

Sigel et al. "The Mechanism of Blood Vessel Closure by High Frequency Electrocoagulation"; Surgery Gynecology & Obstetrics, Oct. 1965 pp. 823-831.

Sampayan et al, "Multilayer Ultra-High Gradient Insulator Technology"; Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy"; The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females"; Current Surgical Techniques in Urology, vol. 14, Issue 3, 2001.

Palazzo et al. "Randomized clinical trial of Ligasure versus open haemorrhoidectomy"; British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room"; Sales/Product Literature 2001.

Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery"; Section of HPB Surger, Nashington University School of Medicine, St. Louis MO, Presented at AHPBA, Feb. 2001.
Sayfan et al. "Sutureless Closed Hemorrhoidectomy: A New Technique"; Annals of Surgery vol. 234 No. 1 Jul. 2001; pp. 21-24.
Levy et al., "Update on Hysterectomy—New Technologies and Techniques"; OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al. "Vessel Sealing for Hemostasis During Pelvic Surgery"; Int'l Federation of Gynecology and Obstetrics FIGO World Congress 2000, Washington, D.C.
McLellan et al. "Vessel Sealing for Hemostasis During Gynecologic Surgery"; Sales/Product Literature 1999.
U.S. Appl. No. 0/387,883, filed Sep. 1, 1999, inventor: Schmaltz.
U.S. Appl. No. 09/591,328, filed Jun. 9, 2000; inventor: Ryan.
U.S. Appl. No. 12/336,970, filed Dec. 17, 2008; inventor: Sremcich.
Partial European Search Report issued in con-esponding application No. 17184186.9 dated Oct. 13, 2017.
Extended European Search Report issued in corresponding application No. 17184186.9 dated Jan. 24, 2018.

\* cited by examiner

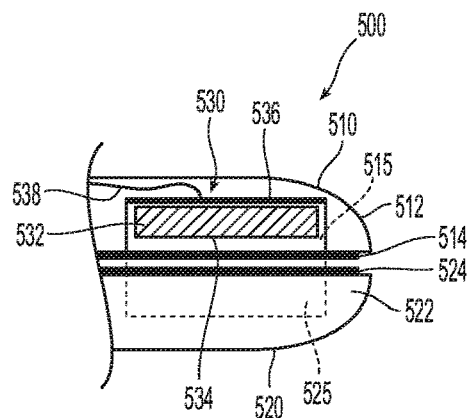
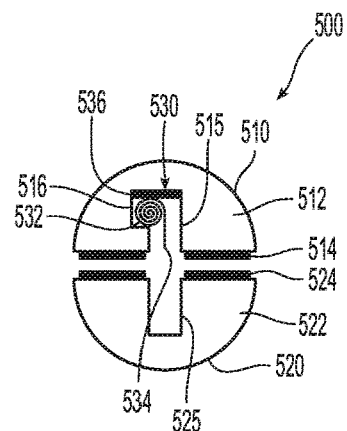
Fig. 8A  Fig. 8B
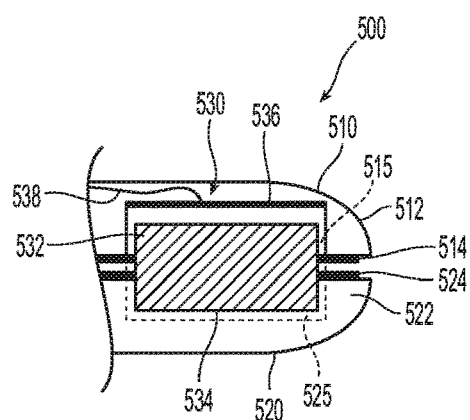
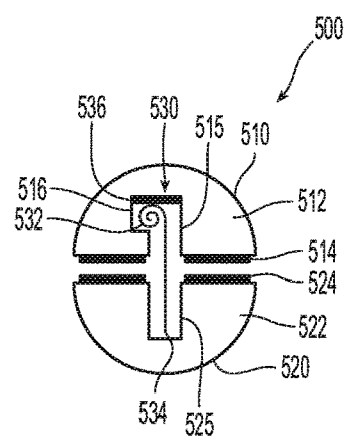
Fig. 9A  Fig. 9B
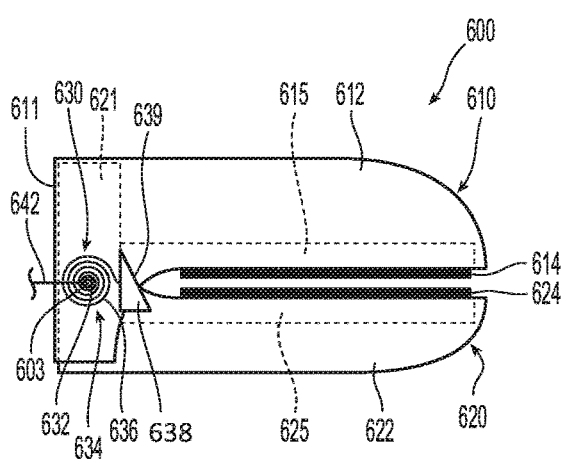
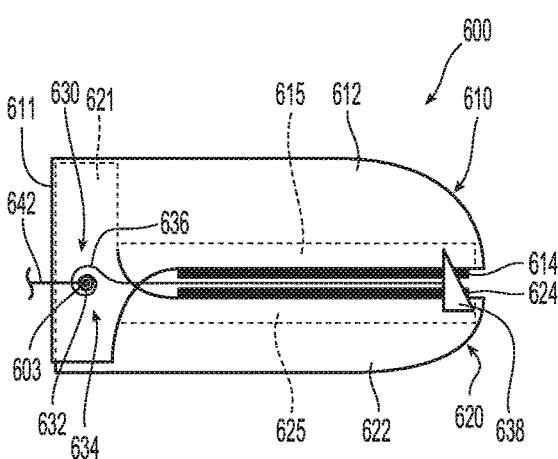
Fig. 10  Fig. 11

CUTTING MECHANISMS FOR SURGICAL END EFFECTOR ASSEMBLIES, INSTRUMENTS, AND SYSTEMS

CROSS REFERENCE TO RELATED APPLICATION

The present application claims the benefit of and priority to U.S. Provisional Application Ser. No. 62/369,958, filed on Aug. 2, 2016, the entire contents of which are incorporated herein by reference.

BACKGROUND

Technical Field

The present disclosure relates to surgical devices and, more particularly, to cutting mechanisms for use with surgical end effector assemblies, instruments, and systems.

Background of Related Art

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

In accordance with aspects of the present disclosure, an end effector assembly configured for use with a surgical instrument or surgical system is provided. The end effector assembly includes first and second jaw members each including an outer jaw housing, a tissue-treating plate, and a longitudinally-extending channel defined therethrough. At least one of the first or second jaw members is pivotable relative to the other between a spaced-apart position and an approximated position. A cutting mechanism is also provided. The cutting mechanism includes an activation member extending longitudinally through at least a portion of the longitudinally-extending channel of the second jaw member. The activation member is configured to move from a substantially linear configuration to an arced configuration. A knife is disposed on the activation member and configured such that, in the substantially linear configuration of the activation member, the knife is fully disposed within the longitudinally-extending channel of the second jaw member, and such that, in the arced configuration of the activation member, the knife extends transversely from the longitudinally-extending channel of the second jaw member, between the first and second jaw members, and at least partially into the longitudinally-extending channel of the first jaw member.

In an aspect of the present disclosure, the activation member is electrically coupled to a source of energy. In such aspects, upon energizing the activation member, the activation member is moved from the substantially linear configuration to the arced configuration.

In another aspect of the present disclosure, the activation member is formed from a material selected from the group consisting of: an electro-active polymer, an electrically-activated shape-memory metal, an electromagnetic material, and a bimetallic material.

In still another aspect of the present disclosure, proximal and distal ends of the activation member are fixed relative to the second jaw member.

In yet another aspect of the present disclosure, the activation member includes a flat spring biased towards the substantially linear configuration.

In still yet another aspect of the present disclosure, the cutting mechanism further includes a pull-wire operably coupled to the flat spring. In such aspects, actuation of the pull-wire urges the flat spring from the substantially linear configuration to the arced configuration.

In another aspect of the present disclosure, the flat spring includes a proximal end fixed relative to the second jaw member and a distal end coupled to the pull-wire.

An end effector assembly configured for use with a surgical instrument or surgical system provided in accordance with aspects of the present disclosure includes first and second jaw members each including an outer jaw housing, a tissue-treating plate, and a longitudinally-extending channel defined therethrough. At least one of the first or second jaw members is pivotable relative to the other between a spaced-apart position and an approximated position. A cutting mechanism is also provided including an elongated sheet defining a cutting edge and extending longitudinally through at least a portion of the longitudinally-extending channel of the first jaw member. The elongated sheet is initially disposed in a rolled-up configuration, wherein the elongated sheet is fully disposed within the longitudinally-extending channel of the first jaw member. A heating element is disposed within the longitudinally-extending channel of the first jaw member and configured to heat the elongated sheet to move the elongated sheet from the rolled-up configuration to an un-rolled configuration, wherein, the cutting edge of the elongated sheet extends transversely from the longitudinally-extending channel of the first jaw member, between the first and second jaw members, and at least partially into the longitudinally-extending channel of the second jaw member.

In an aspect of the present disclosure, the heating element is electrically coupled to a source of energy. In such aspects, energizing the heating element produces heat to the elongated sheet.

In another aspect of the present disclosure, the heating element includes at least one resistive heating element.

In yet another aspect of the present disclosure, the elongated sheet, in the rolled-up configuration, is disposed within an enlarged portion of the longitudinally-extending channel of the first jaw member.

In still another aspect of the present disclosure, the elongated sheet is formed from a bimetallic material.

Another end effector assembly configured for use with a surgical instrument or surgical system and provided in accordance with the present disclosure includes first and second jaw members each including a proximal flange, a distal body, a tissue-treating plate disposed on the distal body, and a longitudinally-extending channel defined through the distal body. A pivot pin pivotably couples the proximal flanges of the first and second jaw members such that at least one of the first or second jaw members is pivotable relative to the other between a spaced-apart position and an approximated position. A cutting mechanism is also provided, including a clutch mechanism disposed about the pivot pin and transitionable between an engaged condition and a disengaged condition, a spring having a first end engaged to the clutch mechanism and a second free end, and a knife proximate the second free end of the spring. The clutch mechanism is initially disposed in the engaged condition with the spring wound-up about the clutch mechanism such that the knife is positioned proximally of the distal bodies of the first and second jaw members. Upon transition of the clutch mechanism to the disengaged condition, the spring unwinds and extends distally so as to urge the knife distally between the first and second jaw members and through the longitudinally-extending channels thereof.

In an aspect of the present disclosure, the spring is biased towards an extended position such that, upon disengagement of the clutch mechanism, the spring unwinds and extends distally under the bias thereof.

In another aspect of the present disclosure, the cutting mechanism further includes a pull-wire operably coupled to the clutch mechanism. In such aspects, actuation of the pull-wire transitions the clutch mechanism from the engaged condition to the disengaged condition.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and:

FIG. 8A is a longitudinal, cross-sectional view of another end effector assembly provided in accordance with the present disclosure and configured for use with the forceps of FIG. 1A, the forceps of FIG. 2, the system of FIG. 3, or any other suitable surgical instrument, wherein the knife thereof is disposed in a retracted position;

FIG. 8B is a transverse, cross-sectional view of the end effector assembly of FIG. 8A, wherein the knife thereof is disposed in the retracted position;

FIG. 9A is a longitudinal, cross-sectional view of the end effector assembly of FIG. 8A, wherein the knife thereof is disposed in an extended position;

FIG. 9B is a transverse, cross-sectional view of the end effector assembly of FIG. 9A, wherein the knife thereof is disposed in the extended position;

FIG. 10 is a longitudinal, cross-sectional view of another end effector assembly provided in accordance with the present disclosure and configured for use with the forceps of FIG. 1A, the forceps of FIG. 2, the system of FIG. 3, or any other suitable surgical instrument, wherein the knife thereof is disposed in a retracted position; and FIG. 11 is a longitudinal, cross-sectional view of the end effector assembly of FIG. 10, wherein the knife thereof is disposed in an extended position.

DETAILED DESCRIPTION

Figure 1A:
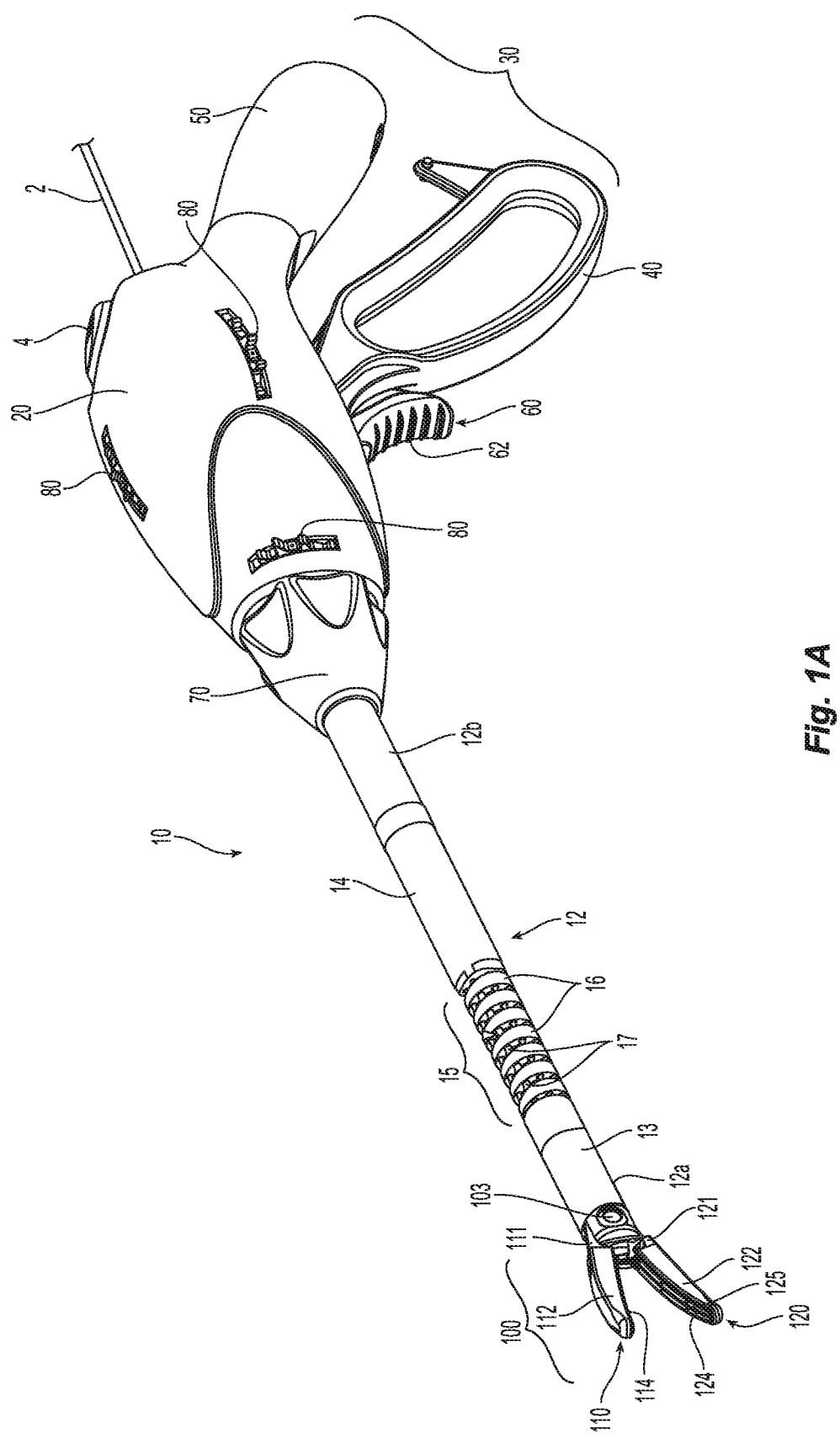
FIG. 1A is a perspective view of endoscopic surgical forceps exemplifying the aspects and features of the present disclosure, wherein the shaft of the endoscopic surgical forceps is disposed in a non-articulated position and wherein the jaw members of the endoscopic surgical forceps are disposed in a spaced-apart position.
Figure 1B:
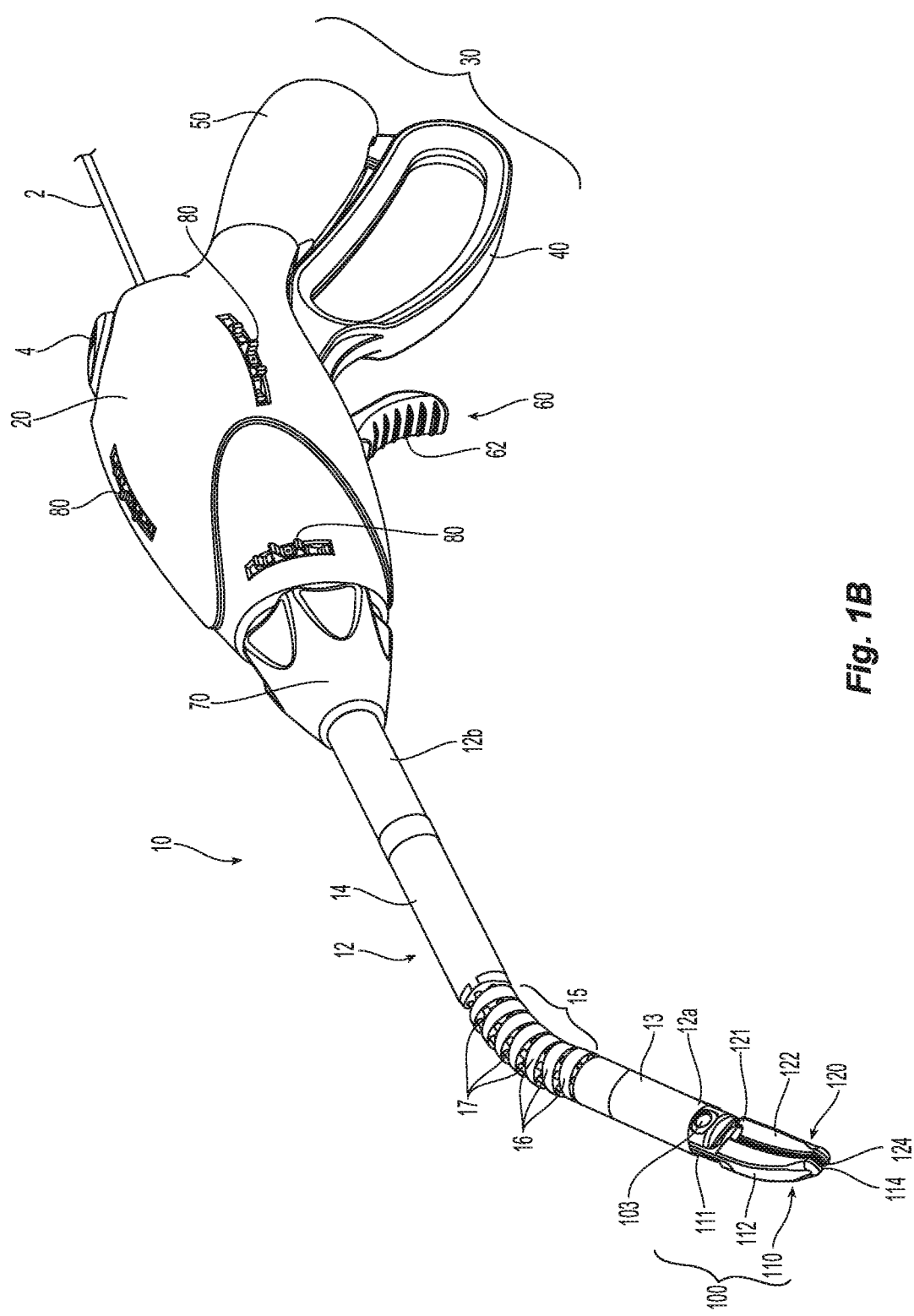
FIG. 1B is a perspective view of the endoscopic surgical forceps of FIG. 1A, wherein the shaft of the endoscopic surgical forceps is disposed in an articulated position and wherein the jaw members of the endoscopic surgical forceps are disposed in an approximated position.

Referring generally to FIGS. 1A and 1B, an endoscopic surgical forceps exemplifying the aspects and features of the present disclosure is shown generally identified by reference numeral 10. For the purposes herein, endoscopic surgical forceps 10 is generally described. Aspects and features of endoscopic surgical forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a plurality of articulation actuators 80, an activation switch 4, and an end effector assembly 100. Forceps 10 further includes a shaft 12 having a distal end 12a configured to mechanically engage end effector assembly 100 and a proximal end 12b that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 of jaw members 110, 120, respectively, of end effector assembly 100. Activation switch 4 is coupled to tissue-treating plates 114, 124 and the source of energy for selectively activating the supply of energy to jaw members 110, 120 for treating, e.g., cauterizing, coagulating/desiccating, and/or sealing, tissue.

Shaft 12 of forceps 10 defines a distal segment 13 positioned towards distal end 12a thereof, a proximal segment 14 positioned towards proximal end 12b thereof, and an articulating section 15 disposed between the distal and proximal segments 13, 14, respectively. Articulating section 15 includes a plurality of articulating links 16 having a plurality of articulation cables 17 extending therethrough. Each cable 17 is operably engaged at its distal end to distal segment 13 and at its proximal end to one of the articulation actuators 80 so as to enable articulation of distal segment 13 and, thus, end effector assembly 100, relative to proximal segment 14 upon actuation of one or more of articulation actuators 80. In some embodiments, articulating section 15 and articulation actuators 80 are omitted, such that shaft 12 of forceps 10 does not articulate. In either configuration, rotating assembly 70 operably couples shaft 12 to housing 20 so as to enable selective rotation of shaft 12 and, thus, end effector assembly 100, relative to housing 20.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both jaw members 110, 120 of end effector assembly 100 about a pivot 103 between a spaced-apart position (FIG. 1A) and an approximated position (FIG. 1B) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 1B).

Trigger assembly 60 includes a trigger 62 coupled to housing 20 and movable relative thereto between an un-actuated position and an actuated position. Trigger 62 is operably coupled to a cutting mechanism, various embodiments of which are detailed below, so as to actuate the cutting mechanism to cut tissue grasped between jaw members 110, 120 of end effector assembly 100 upon actuation of trigger 62. As an alternative to a pivoting trigger 62, a slide trigger, push-button, toggle switch, or other suitable actuator may be provided.

End effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 and the source of energy (not shown), e.g., via the wires (not shown) extending from cable 2 through forceps 10, such that energy may be selectively supplied to tissue-treating plate 114 and/or tissue-treating plate 124 and conducted therebetween and through tissue disposed between jaw members 110, 120 to treat tissue. One or both of jaw members 110, 120 may further define a longitudinally-extending channel 125 (only the channel of jaw member 120 is shown).

Figure 2:
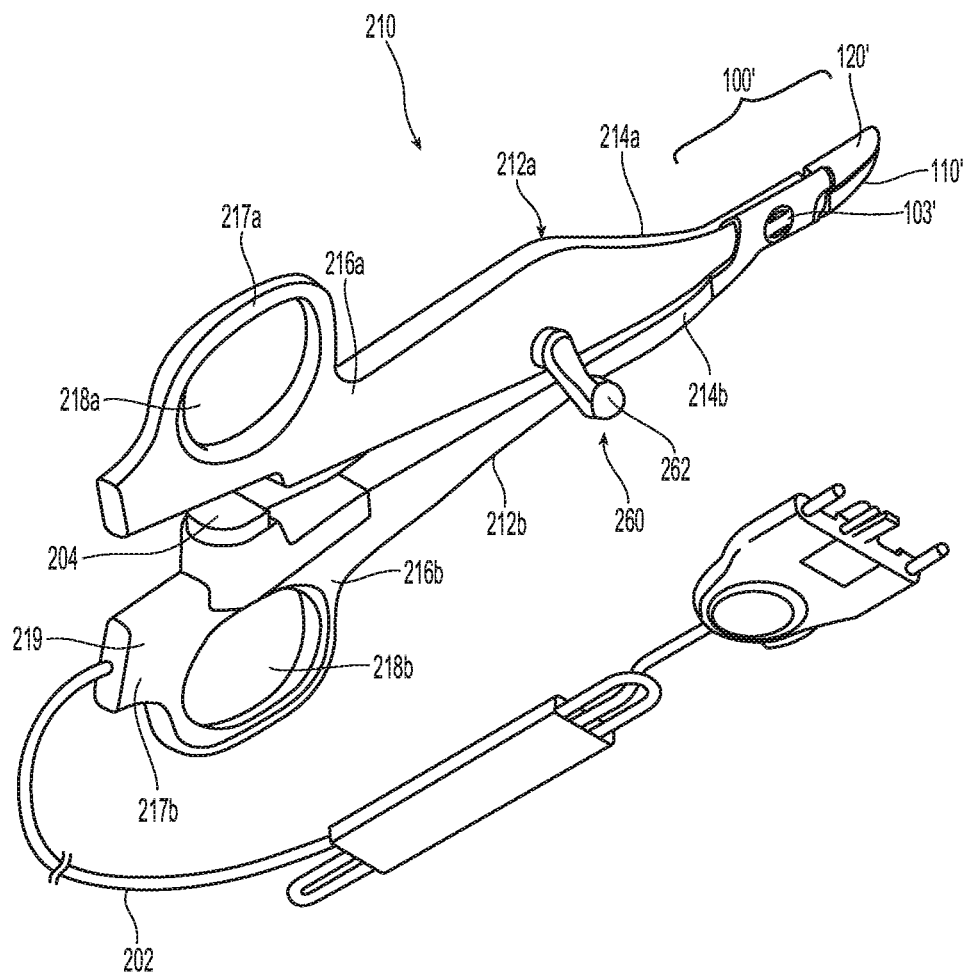
FIG. 2 is a perspective view of an open surgical forceps exemplifying the aspects and features of the present disclosure.

Referring to FIG. 2, an open surgical forceps exemplifying the aspects and features of the present disclosure is shown generally identified by reference numeral 210. For the purposes herein, open surgical forceps 210 is generally described. Aspects and features of open surgical forceps 210 not germane to the understanding of the present disclosure are omitted to avoid obscuring the aspects and features of the present disclosure in unnecessary detail.

Forceps 210 includes two elongated shaft members 212a, 212b, each having a proximal end 216a, 216b, and a distal end 214a, 214b, respectively. Forceps 210 is configured for use with an end effector assembly 100' similar to end effector assembly 100 (FIGS. 1A and 1B). More specifically, end effector assembly 100' includes first and second jaw members 110', 120' attached to respective distal ends 214a, 214b of shaft members 212a, 212b. Jaw members 110', 120' are pivotably connected about a pivot 103'. Each shaft member 212a, 212b includes a handle 217a, 217b disposed at the proximal end 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy (not shown), e.g., a generator. Proximal shaft connector 219 secures a cable 202 to forceps 210 such that the user may selectively supply energy to jaw members 110', 120' for treating tissue and for energy-based tissue cutting. More specifically, an activation switch 204 is provided for supplying energy to jaw members 110', 120' to treat tissue upon sufficient approximation of shaft members 212a, 212b, e.g., upon activation of activation switch 204 via shaft member 212a.

Forceps 210 further includes a trigger assembly 260 including a trigger 262 coupled to one of the shaft members, e.g., shaft member 212a, and movable relative thereto between an un-actuated position and an actuated position. Trigger 262 is operably coupled to a cutting mechanism, various embodiments of which are detailed below, so as to actuate the cutting mechanism to cut tissue grasped between jaw members 110,' 120' of end effector assembly 100' upon movement of trigger 262 to the actuated position. Similarly as noted above, other suitable actuators for the cutting mechanism are also contemplated.

Figure 3:
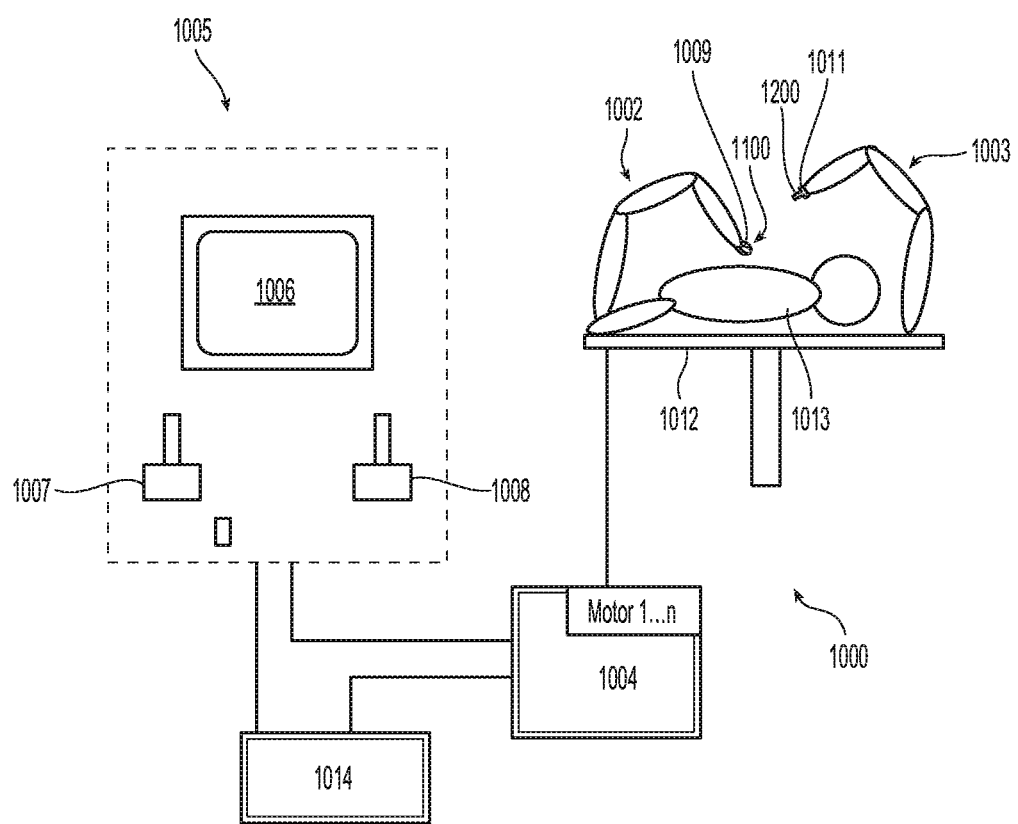
FIG. 3 is a schematic illustration of a robotic surgical system exemplifying the aspects and features of the present disclosure.

Referring generally to FIG. 3, a robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assemblies 100, 100' (FIGS. 1A-1B and 2, respectively), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Referring generally to FIGS. 4A-11, as can be appreciated, design challenges are presented in incorporating cutting mechanisms, particularly those including elongated cutting elements, into surgical instruments having articulating shafts, e.g., forceps 10 (FIGS. 1A and 1B), open surgical instruments, e.g., forceps 210 (FIG. 2), and/or robotic surgical systems, e.g., robotic surgical system 1000 (FIG. 3). Accordingly, the various embodiments of cutting mechanisms detailed below with respect to FIGS. 4A-11 are configured to eliminate the need for elongated cutting elements, thus enabling use with articulating surgical instruments, open surgical instruments, robotic surgical systems, and any other suitable surgical instrument or system.

With reference to FIGS. 4A-5B, an end effector assembly provided in accordance with the present disclosure and configured for use with forceps 10 (FIGS. 1A-1B), forceps 210 (FIG. 2), robotic surgical system 1000 (FIG. 3), and/or any other suitable surgical instrument or system is shown generally identified by reference numeral 300.

Figure 4B:
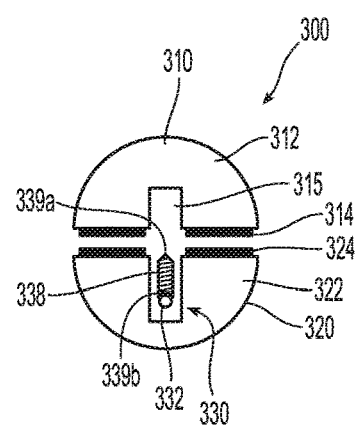
FIG. 4B is a transverse, cross-sectional view of the end effector assembly of FIG. 4A, wherein the knife thereof is disposed in the retracted position.
Figure 5A:
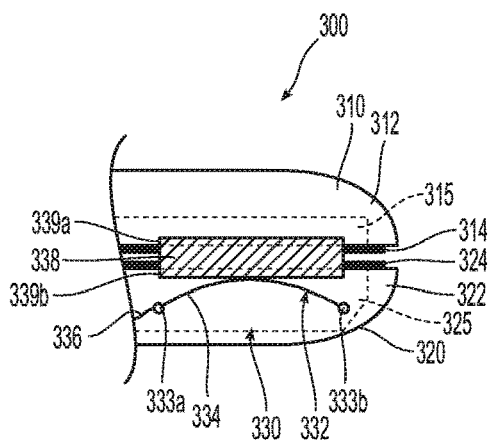
FIG. 5A is a longitudinal, cross-sectional view of the end effector assembly of FIG. 4A, wherein the knife thereof is disposed in an extended position.
Figure 5B:
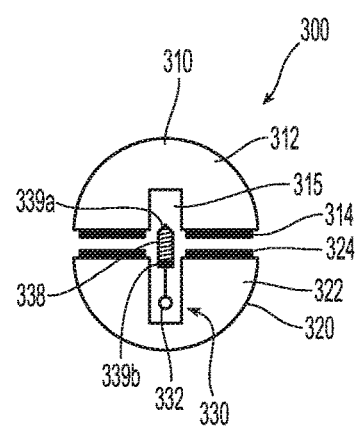
FIG. 5B is a transverse, cross-sectional view of the end effector assembly of FIG. 4A, wherein the knife thereof is disposed in the extended position.

End effector assembly 300 is similar to end effector assemblies 100, 100', 1100 (FIGS. 1A-1B, 2, 3, respectively) and, thus, only differences therebetween will be described in detail below for purposes of brevity. End effector assembly 300 includes first and second jaw members 310, 320 each including a jaw housing 312, 322 and a tissue-treating plate 314, 324. At least one of jaw members 310, 320 defines a longitudinally-extending channel 315, 325 (FIGS. 4B and 5B, respectively).

One of the jaw members, e.g., jaw member 320, includes a cutting mechanism 330 disposed therein. Cutting mechanism 330 includes an activation wire 332, an electrical lead 336, and a knife 338. Activation wires 332 extend longitudinally through channel 325 of jaw member 320. Activation wire 332 is fixed relative to jaw member 320 at proximal and distal ends 333a, 333b, respectively, thereof and includes a body portion 334 extending between the respective proximal and distal ends 333a, 333b thereof. Body portion 334 of activation wire 332 may be configured as a thin strip of material, a cable defining a circular cross-section, or may define any other suitable configuration.

Electrical lead 336 of cutting mechanism 330 is electrically coupled to activation wire 332 for selectively supplying energy thereto. Electrical lead 336 may extend proximally from end effector assembly 300 through and/or around articulating components, pivoting components, and/or other components of the surgical instrument or system used with end effector assembly 300. Electrical lead 336 defines a flexible configuration to avoid interrupting articulation, pivoting, etc. of the surgical instrument or system. Electrical lead 336 may ultimately be coupled to an energy source (not shown) within the housing of the surgical instrument, an external energy source, or other suitable energy source. The actuator, e.g., trigger, of the surgical instrument may be operably coupled to the energy source and/or electrical lead 336 so as to supply energy to activation wire 332 via electrical lead 336 upon actuation of the trigger, and to stop the supply of energy along electrical lead 336 to activation wire 332 upon return of the trigger to an un-actuated position.

Figure 4A:
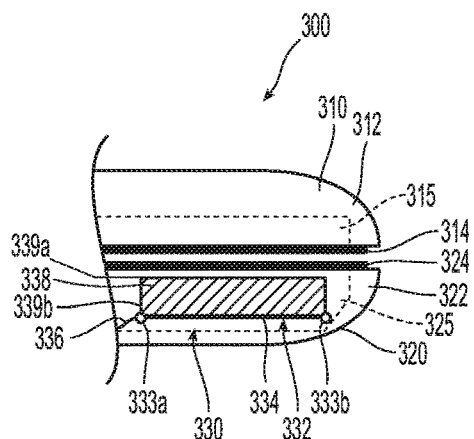
FIG. 4A is a longitudinal, cross-sectional view of an end effector assembly provided in accordance with the present disclosure and configured for use with the forceps of FIG. 1A, the forceps of FIG. 2, the system of FIG. 3, or any other suitable surgical instrument, wherein the knife thereof is disposed in a retracted position.

Activation wire 332, in the absence of energy being supplied thereto, defines a generally linear configuration, as illustrated in FIG. 4A. Upon energization, activation wire 332 is transitioned to an arc-shaped configuration, as illustrated in FIG. 5A. Activation wire 332 may be formed from an electro-active polymer, an electrically-activated shape-memory metal, an electromagnetic material, a bimetallic material, combinations thereof, and/or any other suitable material(s) capable of transitioning between a generally linear configuration and an arc-shaped configuration in response to energization thereof.

Cutting mechanism 330, as noted above, further includes a knife 338 disposed atop activation wire 332 and within longitudinally-extending channel 325 of jaw member 320. Knife 338 defines a longitudinally-extending cutting edge 339a oriented towards jaw member 310 and may be freely seated atop activation wire 332 or may include a base 339b coupled to activation wire 332 in any suitable fashion, e.g., adhesive, welding, mechanical fastening, etc. Knife 338 may define a length that extends a substantial portion of the length of jaw member 320, e.g., between 50% and 90% of the length thereof. Knife 338 is initially disposed in a retracted position (FIGS. 4A and 4B), corresponding to the un-energized, generally-linear configuration of actuation wire 332, wherein knife 338 is disposed within channel 325 and does not extend beyond tissue-treating plate 324. Knife 338 is deployable, upon energization of actuation wire 332, from the retracted position to an extended position (FIGS. 5A and 5B), corresponding to the energized, arc-shaped configuration of actuation wire 332, wherein actuation wire 332 urges knife 338 to extend from channel 325, between tissue-treating plates 314, 324, and at least partially into channel 315 of jaw member 310 to cut tissue grasped between jaw members 310, 320. More specifically, upon the supply of energy via electrical lead 336 to actuation wire 332, actuation wire 332 is arced such that an apex thereof is expanded towards the open end of channel 325 (see FIG. 5A). The arcing of actuation wire 332, in turn, urges knife 338 from the retracted position (FIGS. 4A and 4B) to the extended position (FIGS. 5A and 5B) to cut tissue grasped between jaw members 310, 320.

When the supply of energy to actuation wire 332 is stopped and actuation wire 332 is no longer energized, actuation wire 332 returns to its original, generally-linear configuration, thus allowing or pulling knife 338 back to the retracted position (FIGS. 4A and 4B).

In some embodiments, electrical lead 336 may be coupled to either of the wires (not shown) supplying energy to tissue-treating plates 314, 324 or an activation button (not shown) for initiating the supply of energy to tissue-treating plates 314, 324 such that energy is supplied to actuation wire 332 to electrical lead 336 in cooperation with the initiation of the supply of energy to tissue-treating plates 314, 324. In such embodiments, the supply of energy to activation wire 332 may be delayed and/or activation wire 332 may be configured such that the transitioning of activation wire 332 from the generally linear configuration to the arced configuration is of sufficiently long duration that knife 338 is not urged to extend from channel 325 of jaw member 320 until the tissue grasped between jaw members 310, 320 has been sufficiently treated, e.g., sealed. This ensures that tissue is sufficiently treated before knife 338 is deployed to cut the treated tissue.

Figure 6:
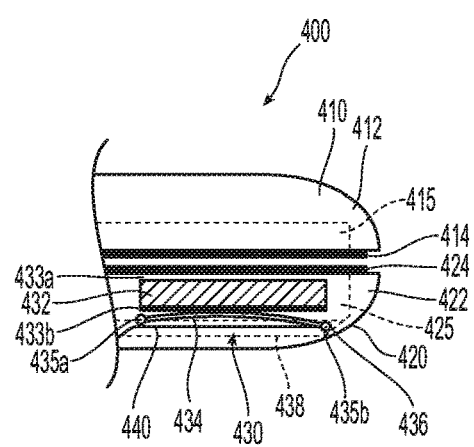
FIG. 6 is a longitudinal, cross-sectional view of another end effector assembly provided in accordance with the present disclosure and configured for use with the forceps of FIG. 1A, the forceps of FIG. 2, the system of FIG. 3, or any other suitable surgical instrument, wherein the knife thereof is disposed in a retracted position.
Figure 7:
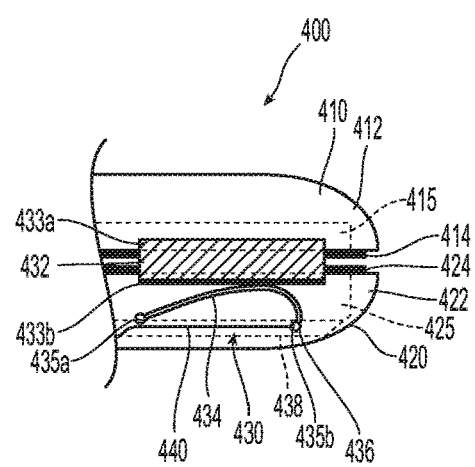
FIG. 7 is a longitudinal, cross-sectional view of the end effector assembly of FIG. 6, wherein the knife thereof is disposed in an extended position.

With reference to FIGS. 6 and 7, an end effector assembly provided in accordance with the present disclosure and configured for use with forceps 10 (FIGS. 1A-1B), forceps 210 (FIG. 2), robotic surgical system 1000 (FIG. 3), and/or any other suitable surgical instrument or system is shown generally identified by reference numeral 400.

End effector assembly 400 is similar to end effector assembly 300 (FIGS. 4A-5B) and, thus, only differences therebetween will be described in detail below for purposes of brevity. End effector assembly 400 includes first and second jaw members 410, 420 each including a jaw housing 412, 422 and a tissue-treating plate 414, 424. At least one of jaw members 410, 420 includes a longitudinally-extending channel 415, 425.

One of the jaw members, e.g., jaw member 420, includes a cutting mechanism 430 disposed therein. Cutting mechanism 430 includes a knife 432, a flat spring 434, a pin 436, a pair of guide tracks 438, and a pull-wire 440. Knife 432 is disposed within channel 425 of jaw member 420 and defines a longitudinally-extending cutting edge 433a oriented towards jaw member 410. Knife 432 may define a length that extends a substantial portion of the length of jaw member 320, e.g., between 50% and 90% of the length thereof. Knife 432 is initially disposed in a retracted position (FIG. 6), wherein knife 432 is disposed within channel 425 and does not extend beyond tissue-treating plate 424. Knife 432 is deployable from the retracted position to an extended position (FIG. 7), wherein knife 432 extends from channel 425, between tissue-treating plates 414, 424, and at least partially into channel 415 of jaw member 410 to cut tissue grasped between jaw members 410, 420.

Flat spring 434 is disposed within channel 425 of jaw member 420 and defines a proximal end 435a fixed relative to jaw member 420 and a free distal end 435b. Flat spring 434 is biased towards a generally linear configuration (FIG. 6) and is resiliently flexible from the generally linear configuration to an arced configuration (FIG. 7), as detailed below. Knife 432 may be freely seated atop flat spring 434 or may include a base 433b coupled to flat spring 434 in any suitable fashion, e.g., adhesive, welding, mechanical fastening, etc.

Pin 436 is engaged to the free distal end 435b of flat spring 434 and extends transversely relative to jaw member 420 and channel 425. More specifically, the free ends of pin 436 are slidably disposed within guide tracks 438, which are defined within the opposed longitudinally-extending walls of jaw member 420 that define channel 425. Guide tracks 438 guide pin 436 longitudinally through channel 425 and relative to jaw member 420.

Pull-wire 440 is engaged to free distal end 435b of flat spring 434 and/or pin 436 at the distal end of pull-wire 440 and extends proximally through jaw member 420. Pull-wire 440 may extend proximally from end effector assembly 400 through and/or around articulating components, pivoting components, and/or other components of the surgical instrument or system used with end effector assembly 400. Pull-wire 440 defines a flexible configuration so as not to be interrupted by or interrupt articulation, pivoting, etc. of the surgical instrument or system used with end effector assembly 400. The actuator, e.g., trigger, of the surgical instrument or system used with end effector assembly 400 may be operably coupled to pull-wire 440 such that, upon actuation of the trigger, pull-wire 440 is pulled proximally. Alternatively, in embodiments where a robotic system is utilized, pull-wire 440 may be coupled to the appropriate cable and motor such that, upon actuation of the motor, pull-wire 440 is pulled proximally.

Pull-wire 440 is initially disposed in a minimally-tensioned condition such that flat spring 434 is biased towards the generally linear configuration (FIG. 6). In the minimally-tensioned condition of pull-wire 440 and the generally linear configuration of flat spring 434, knife 432 is disposed in the retracted position (FIG. 6). Pull-wire 440 is configured to be pulled proximally to thereby pull pin 436 proximally through channel 425 and guide channels 438. As a result of this proximal pulling of pull-wire 440, the free distal end 435b of flat spring 434 is pulled proximally relative to the fixed proximal end 435a thereof such that flat spring 434 is resiliently flexed from the generally linear configuration (FIG. 6) to the arced configuration (FIG. 7). As flat spring 434 is flexed to the arced condition, an apex thereof is expanded towards the open end of channel 425 to urge knife 432 from the retracted position (FIG. 6) to the extended position (FIG. 7) to cut tissue grasped between jaw members 410, 420.

Upon release or return of pull-wire 440, flat spring 434 is returned, under bias, back to the generally linear configuration thereof, thus allowing or pulling knife 432 back to the retracted position.

With reference to FIGS. 8A-9B, an end effector assembly provided in accordance with the present disclosure and configured for use with forceps 10 (FIGS. 1A-1B), forceps 210 (FIG. 2), robotic surgical system 1000 (FIG. 3), and/or any other suitable surgical instrument or system is shown generally identified by reference numeral 500.

End effector assembly 500 is similar to end effector assemblies 100, 100', 1100 (FIGS. 1A-1B, 2, 3, respectively) and, thus, only differences therebetween will be described in detail below for purposes of brevity. End effector assembly 500 includes first and second jaw members 510, 520 each including a jaw housing 512, 522 and a tissue-treating plate 514, 524. At least one of the jaw members 510, 520 includes a longitudinally-extending channel 515, 525 (FIGS. 8B and 9B).

One of the jaw members, e.g., jaw member 510, includes a cutting mechanism 530 housed within jaw housing 512 thereof. Cutting mechanism 530, more specifically, is disposed within an enlarged portion 516 of channel 515 of jaw member 510 and includes an elongated sheet 532 extending longitudinally through enlarged portion 516 of channel 515 of jaw member 510. Elongated sheet 532 may define a length that extends a substantial portion of the length of jaw member 510, e.g., between 50% and 90% of the length thereof. Elongated sheet 532 defines a cutting edge 534 and is initially disposed in a rolled-up configuration (FIGS. 8A and 8B), wherein cutting edge 534 is disposed within channel 515 and does not extend beyond tissue-treating plate 514. Elongated sheet 532 is transitionable from this rolled-up configuration to an un-rolled configuration (FIGS. 9A and 9B), wherein elongated sheet 532 is at least partially un-rolled so as to extend elongated sheet 532, lead by cutting edge 534, between tissue-treating plates 514, 524, and at least partially into channel 525 of jaw member 510 to cut tissue grasped between jaw members 510, 520. Elongated sheet 532 is formed from a bimetallic material, a thermally-activated shape-memory metal, combinations thereof, and/or any other suitable material(s) capable of transitioning between the rolled-up configuration and the un-rolled configuration.

Cutting mechanism 530 further includes a heating element 536 disposed within enlarged portion 516 of channel 515 and an electrical lead 538 operably coupled to heating element 536. Heating element 536 may include one or more resistive heating elements, or other suitable components configured to generate heat in response to application of electrical energy thereto, e.g., via electrical lead 538. Heating element 536 may be disposed on one or more of the inwardly-facing surfaces of jaw housing 512 that defines channel 515, or may define any other suitable configuration to facilitate heating of elongated sheet 532 in order to transition elongated sheet 532 from the rolled-up configuration to the un-rolled configuration.

Electrical lead 538 of cutting mechanism 530 may extend proximally from end effector assembly 500 through and/or around articulating components, pivoting components, and/or other components of the surgical instrument or system used with end effector assembly 500. Electrical lead 538 defines a flexible configuration so as not to be interrupted by or interrupt articulation, pivoting, etc. of the surgical instrument or system. Electrical lead 538 may ultimately be coupled to an energy source (not shown) within the housing of the surgical instrument, an external energy source, or other suitable energy source. The actuator, e.g., trigger, of the surgical instrument may be operably coupled to the energy source and/or electrical lead 538 so as to supply energy to heating element 536 via electrical lead 538 upon actuation of the trigger, and to stop the supply of energy along electrical lead 538 to heating element 536 upon return of the trigger to an un-actuated position.

As noted above, elongated sheet 532 is initially disposed in the rolled-up configuration (FIGS. 8A and 8B), corresponding to an ambient temperature condition of heating element 536, wherein cutting edge 534 is disposed within channel 515 and does not extend beyond tissue-treating plate 514. Upon activation of cutting mechanism 530, energy is supplied to heating element 536 via electrical lead 538 such that heating element 536, in turn, generates heat to ultimately heat elongated sheet 532 sufficiently to transition elongated sheet 532 from the rolled-up configuration to the un-rolled configuration (FIGS. 9A and 9B). As also noted above, this un-rolling of elongated sheet 532 urges cutting edge 534 of elongated sheet 532 to extend between tissue-treating plates 514, 524 and at least partially into channel 525 of jaw member 510 to cut tissue grasped between jaw members 510, 520.

When the supply of energy to heating element 536 is stopped, heating element 536 stops producing heat, thus allowing elongated sheet 532 to cool back down to ambient temperature. Upon such cooling of elongated sheet 532, elongated sheet 532 is returned from the un-rolled configuration (FIGS. 9A and 9B) back to the rolled-up configuration (FIGS. 8A and 8B), such that cutting edge 534 of elongated sheet 532 is returned to within channel 515 of jaw member 510.

With reference to FIGS. 10 and 11, an end effector assembly provided in accordance with the present disclosure and configured for use with forceps 10 (FIGS. 1A-1B), forceps 210 (FIG. 2), robotic surgical system 1000 (FIG. 3), and/or any other suitable surgical instrument or system is shown generally identified by reference numeral 600.

End effector assembly 600 is similar to end effector assemblies 100, 100', 1100 (FIGS. 1A-1B, 2, 3, respectively) and, thus, only differences therebetween will be described in detail below for purposes of brevity. End effector assembly 600 includes first and second jaw members 610, 620 each including a proximal flange 611, 621, a distal body 612, 622, a tissue-treating plate 614, 624 disposed on the respective distal body 612, 622, and a longitudinally-extending channel 615, 625 defined through the respective tissue-treating plate 614, 624 and a portion of the corresponding distal body 612, 622. One or both of jaw members 610, 620 is pivotable relative to the other about a pivot pin 603 operably coupled with and extending through proximal flanges 611, 621 of jaw members 610, 620, respectively.

End effector assembly 600 further includes a cutting mechanism 630 housed between proximal flanges 611, 621 of jaw members 610, 620, respectively and disposed about pivot pin 603. Cutting mechanism 630 includes a clutch block 632 disposed about pivot pin 603 and operably coupled thereto so as to define a clutch mechanism 634 therewith. Cutting mechanism 630 further includes a spring 636 engaged to and initially wound about clutch block 632 and pivot pin 603, and a knife 638 engaged at the free distal end of spring 636. Spring 636 is biased towards a linear configuration such that, when spring 636 is wound-up about clutch block 632 and pivot pin 602, spring 636 is disposed in a loaded position. In the initial, wound, loaded position of spring 636, knife 638 is disposed between proximal flanges 611, 621 and does not extend distally to distal bodies 612, 622 of jaw members 610, 620, respectively (see FIG. 10). Knife 638 defines a distal cutting edge 639.

Cutting mechanism 630 may further include a pull-wire 642 operably coupled to clutch block 632 and extending proximally from end effector assembly 600. Pull-wire 642, in embodiments where so provided, extends proximally from end effector assembly 600 through and/or around articulating components, pivoting components, and/or other components of the surgical instrument used with end effector assembly 600. Pull-wire 642 may define a flexible configuration to avoid interrupting articulation, pivoting, etc. of the surgical instrument. Alternatively, pull-wire 642 may be configured as a rigid or semi-rigid rod, in embodiments where the device does not pivot and/or articulate. Pull-wire 642 may ultimately be coupled to an actuator, e.g., trigger, of the surgical instrument or system used therewith such that actuation of the actuator pulls pull-wire 641 proximally. Upon proximal pulling of pull-wire 642, clutch mechanism 634 is disengaged, e.g., clutch block 632 is disengaged from pivot pin 603, such that clutch block 632 is free to rotate about pivot pin 603. With clutch block 632 free to rotate relative to pivot pin 603, spring 636 is urged, under bias, from the initial, wound-up position (FIG. 10) towards a more linear configuration (FIG. 11), wherein the free distal end of spring 636 extends distally from pivot pin 603. As a result of this urging of spring 636, knife 638, led by distal cutting edge 639 is translated distally through channels 615, 625 of jaw members 610, 620 and between tissue-treating plates 614, 624 of jaw members 610, 620 to cut tissue grasped therebetween (see FIG. 11).

As an alternative to pull-wire 642, clutch mechanism 634 may be disengaged in any other suitable manner. For example, the drive mechanism (not shown) configured to pivot jaw member 610 and/or jaw member 620 from the spaced-apart position to the approximated position may further be configured to urge pivot pin 603 (and/or one or both of jaw members 610, 620) to rotate to an over-actuated position, thereby disengaging clutch mechanism 634 and permitting spring 636, under its bias, to translate knife 638 distally between jaw members 610, 620 to cut tissue grasped therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly configured for use with a surgical instrument or surgical system, the end effector assembly comprising:
    first and second jaw members each including an outer jaw housing, a tissue-treating plate, and a longitudinally-extending channel defined therethrough, at least one of the first or second jaw members pivotable relative to the other between a spaced-apart position and an approximated position; and
    a cutting mechanism, including:
        an activation member extending longitudinally through at least a portion of the longitudinally-extending channel of the second jaw member, the activation member configured to move from a substantially linear configuration to an arced configuration, the activation member including a flat spring biased towards the substantially linear configuration; and
        a knife disposed on the activation member, wherein, in the substantially linear configuration of the activation member, the knife is fully disposed within the longitudinally-extending channel of the second jaw member, and wherein, in the arced configuration of the activation member, the knife extends transversely from the longitudinally-extending channel of the second jaw member, between the first and second jaw members, and at least partially into the longitudinally-extending channel of the first jaw member.

2. The end effector assembly according to claim 1, wherein the activation member is electrically coupled to a source of energy and wherein, upon energizing the activation member, the activation member is moved from the substantially linear configuration to the arced configuration.

3. The end effector assembly according to claim 2, wherein the activation member is formed from a material selected from the group consisting of: an electro-active polymer, an electrically-activated shape-memory metal, an electromagnetic material, and a bimetallic material.

4. The end effector assembly according to claim 2, wherein proximal and distal ends of the activation member are fixed relative to the second jaw member.

5. The end effector assembly according to claim 1, wherein the cutting mechanism further includes a pull-wire operably coupled to the flat spring, and wherein actuation of the pull-wire urges the flat spring from the substantially linear configuration to the arced configuration.

6. The end effector assembly according to claim 5, wherein the flat spring includes a proximal end fixed relative to the second jaw member and a distal end coupled to the pull-wire.

\* \* \* \* \*